United States Patent [19]

Sieja

[11] Patent Number: 5,192,399
[45] Date of Patent: Mar. 9, 1993

[54] PURIFICATION OF AMINONITRILES OR DIAMINES

[75] Inventor: James B. Sieja, Wilmington, Del.

[73] Assignee: E. I. Du Pont de Nemours and Company, Wilmington, Del.

[21] Appl. No.: 757,287

[22] Filed: Sep. 10, 1991

Related U.S. Application Data

[63] Continuation-in-part of Ser. No. 648,002, Jan. 30, 1991, abandoned.

[51] Int. Cl.$^5$ .................. B01D 3/10; B01D 3/34; C08F 20/42
[52] U.S. Cl. .................. 203/36; 203/37; 203/91; 203/DIG. 6; 558/452; 558/456; 558/463
[58] Field of Search ............ 203/36, 91, DIG. 6, 203/37; 558/452, 456, 463

[56] References Cited

U.S. PATENT DOCUMENTS

| 2,242,309 | 5/1941 | Lazier et al. | 558/456 |
|---|---|---|---|
| 2,351,157 | 6/1944 | Semon | 203/36 |
| 2,770,645 | 11/1956 | McDonald et al. | 558/463 |
| 3,429,783 | 2/1969 | Campbell et al. | 558/456 |
| 3,442,771 | 5/1969 | Jordan et al. | 203/36 |
| 3,496,212 | 2/1970 | Davison et al. | 203/36 |
| 3,536,593 | 10/1970 | Hurley et al. | 203/36 |
| 3,647,054 | 3/1972 | Tsuboi et al. | 203/36 |
| 3,972,940 | 8/1976 | Morgan, Jr. | 564/492 |
| 3,983,011 | 9/1976 | Wiggill | 203/91 |
| 4,061,858 | 12/1977 | Wild et al. | 558/463 |
| 4,601,859 | 7/1986 | Galle et al. | 564/492 |
| 4,808,344 | 2/1989 | Hallenburg | 203/36 |

FOREIGN PATENT DOCUMENTS

| 0223419 | 6/1958 | Australia | 558/452 |
|---|---|---|---|
| 0562335 | 8/1958 | Canada | 558/463 |
| 1912720 | 10/1969 | Fed. Rep. of Germany | 203/36 |

*Primary Examiner*—Virginia Manoharan
*Attorney, Agent, or Firm*—Earl L. Handley

[57] ABSTRACT

Separation of an aliphatic aminonitrile or an aliphatic diamine from a mixture containing the corresponding cyclic, aliphatic, mono-unsaturated amine by adding caustic compound to the mixture and then distilling the aminonitrile or the diamine at a temperature less than 170° C. and at a pressure of less than 1 atmosphere.

3 Claims, No Drawings

PURIFICATION OF AMINONITRILES OR DIAMINES

REFERENCE TO PRIOR APPLICATION

This application is a continuation-in-part of U.S. patent application Ser. No. 07/648,002 filed Jan. 30, 1991, abandoned.

1. Field of the Invention

This invention relates to the purification of an aliphatic aminonitrile or an aliphatic diamine by distilling it from a mixture containing a cyclic, aliphatic, mono-unsaturated amine. The aminonitrile or diamine is then sufficiently pure to be polymerized to form high molecular weight nylon having good color and a low gel content.

2. Background of the Invention

The polymerization of 6-aminocapronitrile to form nylon polymer is disclosed in Greenwalt U.S. Pat. No. 2,245,129, and Curatolo et al. U.S. Pat. No. 4,568,736.

When 6-aminocapronitrile is produced by partial hydrogenation of adiponitrile, hexamethylene diamine and the cyclic, aliphatic, mono-unsaturated amine, tetrahydroazepine, i.e. the latter compound represented by the formula:

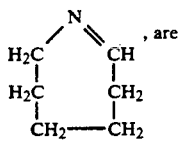, are also coproduced. The tetrahydroazepine (hereinafter sometimes referred to as THA) is not easily separated. The presence of THA in the 6-aminocapronitrile (hereinafter sometimes referred to as 6-ACN) that is to be polymerized limits the molecular weight of the polymer and causes color and branching in the polymer. It is, therefore important that THA be removed from the 6-ACN before polymerization.

A corresponding cyclic, aliphatic, mono-unsaturated amine is formed when the $C_4$, $C_5$, $C_7$ through $C_{12}$ analogs of adiponitrile are partially hydrogenated to form the $C_4$ amino aliphatic nitrile, the $C_5$ amino aliphatic nitrile, and the $C_7$ through $C_{12}$ amino aliphatic nitriles, and when the $C_4$ through $C_{12}$ aliphatic dinitriles are fully hydrogenated to form the corresponding aliphatic diamines.

It is an object of the present invention to provide a simple and efficient method of obtaining $C_4$ to $C_{12}$ aliphatic aminonitriles or $C_4$ to $C_{12}$ aliphatic diamines that are free from the cyclic, aliphatic, mono-unsaturated amine having a corresponding number of carbon atoms.

SUMMARY OF THE INVENTION

This invention is a process for the separation of $C_4$ to $C_{12}$ aliphatic aminonitriles or the corresponding diamines from a mixture which also contains the cyclic, aliphatic, mono-unsaturated amine having a corresponding number of carbon atoms by adding a caustic compound to the mixture and then distilling the aminonitrile or the diamine from the mixture.

The addition of caustic to a mixture appears to shift the equibria involving the mono-unsaturated amine and forms a mono-unsaturated amine reaction product that has a considerably higher boiling point than aliphatic aminonitrile or the diamine, and accordingly the aliphatic aminonitrile or the diamine can now be separated by distillation.

DETAILED DESCRIPTION

The caustic compound used in the process may be one of a variety of bases such as alkali metal hydroxides, some alkaline earth hydroxides, tetraalkylammonium hydroxide, alkali metal alkoxides and alkaline earth metal alkoxides. Specific bases that are useful include: sodium hydroxide, potassium hydroxide, lithium hydroxide, barium hydroxide, tetra butyl ammonium hydroxide, sodium methoxide, potassium ethoxide, and potassium tert-butoxide. The caustic compound may be added to the mixture containing the aliphatic aminonitrile or the diamine and aliphatic cyclic, mono-unsaturated amine as an anhydrous solid, or dispersed on an inert substrate such as silica, or as an aqueous solution. An aqueous solution is preferred when operating on a large scale.

The amount of caustic compound added can vary widely. The caustic compound apparently acts as a catalyst in reacting with the mono-unsaturated amine, so an amount less than a stoichiometric amount is effective. However, an amount somewhat in excess of caustic compound is not harmful; for example, an amount of about 5% in excess of the mono-unsaturated amine. Large excess (four or more times the stoichiometric amount) of caustic compound tends to generate by-products such as 6-aminocaproamide. A preferred range of caustic compound for mixtures normally obtained by hydrogenation of a $C_4$ to $C_{12}$ dinitrile is about 0.025 to 0.5% by weight, based on the aminonitrile or diamine.

The distillation of the aliphatic aminonitrile or diamine from the mixture containing the caustic compound should be carried out at temperatures of less than about 170° C. The pressure of the distillation must be regulated accordingly, i.e. reduced to less than atmospheric pressure. Pressures as high as 100 mm of mercury are operable, but it is preferable to operate at pressures of less than 80 mm of mercury. Good results are obtained at pressures in the range of 10 to 60 mm of mercury, but pressures as low as 0.25 mm of mercury are satisfactory although not attractive for large scale operation.

The process of the present invention is particularly effective when the aliphatic aminonitrile or diamine having 4 to 12 carbon atoms is selected from the group consisting of 4-aminobutyronitrile, 5-aminovaleronitrile, 2-methyl-5-aminovaleronitrile, 6-aminocapronitrile, 12-aminododecanenitrile, 1,4-tetramethylenediamine, 1,5-pentamethylenediamine, 2-methyl-1,5-pentamethylenediamine, 1,6-hexamethylenediamine, 1,12-dodecanediamine, and the cyclic, aliphatic, mono-unsaturated amine having a corresponding number of carbon atoms is selected from the group consisting of dihydropyrrole, tetrahydropyridine, 3-methyltetrahydropyridine, tetrahydroazepine, and mono-unsaturated cyclododecylamine.

EXAMPLES

Example 1

A mixture of 50 ml (about 43 g) of 6-ACN containing 0.23% THA and 1 ml of 50% aqueous sodium hydroxide was heated to 80 deg C. for ½ hr. The 6-ACN was distilled at 0.25 mm Hg, pot temp about 75 deg C., head temp about 60 deg C. Two cuts were taken, with no substantial amount of heel remaining in the pot. The first cut weighed 27 g and contained 0% THA, and the second weighed 16 g and contained 0.039% THA.

Example 2

A mixture of 50 ml (about 43 g) of 6-ACN containing 0.017% THA and 1 ml of 50% aqueous sodium hydroxide was heated to 80 deg C. for ½ hr. The 6-ACN was distilled at 0.25 mm Hg, and two cuts were taken. The first cut weighed 21 g and contained 0% THA, and the second cut weighed 23.6 g and contained 0% THA.

Example 3

A mixture of 150 g of 6-ACN containing 0.22% THA and 1 g of 50% sodium hydroxide was distilled at 40 mm Hg, pot temperature 144 deg C., head temperature 139 deg C. The first cut weighed 67 g and contained 0% THA, the second cut weighed 66 g and contained 0% THA, and the 3rd cut weighed 12 g and contained 0.065% THA.

Control for Example 3

A mixture of 150 g of 6-ACN containing 0.22% THA and 1 g of water (and no added caustic compound) was distilled at 40 mm Hg. The first cut weighed 72 g and contained 0.19% THA, the second cut weighed 66 g and contained 0.25% THA. The pot residue weighed 12.3 g and contained 0.62% THA.

Example 4

A mixture of 150 g 6-ACN containing 0.22% THA and 0.25 g of powdered sodium hydroxide was distilled at 20 mm Hg. Cut 1 weighed 44.8 g and contained 0% THA, cut 2 weighed 45.6 g and contained 0% THA, cut 3 weighed 46 g and contained <0.005% THA, cut 4 weighed 8.6 g and contained 0.063% THA.

Example 5

A 500 cc distillation pot was charged with 250 g of 6-ACN containing 0.22% THA and 0.5 g of 50% aqueous sodium hydroxide. A funnel attached to the distillation pot was charged with 1100 g of 6-ACN containing 0.22% THA. The 6-ACN was distilled at 50 mm, feeding the 6-ACN at the same rate as it was distilling, maintaining the same level of 6-ACN in the pot as was originally present. The first cut weighed 430 g and contained 0% THA, the second weighed 416 g and contained 0% THA, the third weighed 260 g and contained 0.01% THA. A total of 1106 g of 6-ACN were distilled from the 0.5 g of caustic (0.022 wt. % NaOH overall).

Example 6

A mixture of 150 g of 6-ACN containing 0.22% THA and 0.5 g of 50% aqueous potassium hydroxide was distilled at 50 mm Hg. The first cut weighed 45.5 g and contained 0% THA, the second weighed 44.6 g and contained 0.01% THA, the third weighed 44.7 g and contained 0.05% THA.

Example 7

A mixture of 150 g of 6-ACN containing 0.22% THA and 1.5 g of 50% aqueous sodium hydroxide was distilled at 100 mm Hg. Pot temperature was 170 deg C., head temperature was 160 deg C. The first cut weighed 66.4 g and contained 0.018% THA, the second weighed 49 g and contained 0.067% THA, the third weighed 17.4 g and contained 0.64% THA.

Example 8

A mixture of 150 g of 6-ACN containing 0.22% THA and 0.5 g of 50% aqueous sodium hydroxide was distilled at 20 mm Hg. Pot temperature was 133 deg C., head temperature 129 deg C. The first cut weighed 40.9 g and contained 0% THA, the second weighed 46.5 g and contained 0% THA, the third weighed 37.2 g and contained 0% THA, the fourth weighed 15.6 g and contained 0.025% THA.

Control for Example 8

A mixture of 150 g of 6-ACN containing 0.22% THA and 0.25 g water (and no added caustic compound) was distilled at 20 mm Hg. The first cut weighed 43.5 g and analyzed for 0.15% THA, the second weighed 43.9 g and analyzed for 0.20% THA, the third weighed 42.3 g and analyzed for 0.22% THA, the fourth weighed 13.67 g and analyzed for 0.27% THA, the fifth weighed 4.0 g and analyzed for 0.4% THA.

Example 9

Removal of THA from Hexamethylenediamine (HMD)

Four distillations were run. All distillations were made batchwise with 100 grams of 90% HMD (10% water was added to the HMD for dissolution), which contained 530 ppm THA on a 100% HMD basis. Runs 1 and 2 were made with a simple poop-still head. Runs 3 and 4 used a 7 inch Vigreax column. All material was taken overhead, i.e. no reflux returned to the pot. Four cuts were taken in each case. Runs 1 and 3 contained no caustic. Runs 2 and 4 contained 0.1 grams of 50% NaOH (555 ppm NaOH based on 100% HMD).

| RUN | PRESS (mm) | HEAD TEMP deg C. | CUT # | WT (g) | THA (ppm) | CAUSTIC ADDED |
|---|---|---|---|---|---|---|
| 1 | 20 | 99 | 1 | 20 | trace | no |
|   |    |    | 2 | 19 | trace |    |
|   |    |    | 3 | 18 | 80    |    |
|   |    |    | 4 | 24 | 110   |    |
|   |    |    | heel | 6.6 | 2530 |    |
| 2 | 20 | 99 | 1 | 23 | nil | yes |
|   |    |    | 2 | 20 | nil |    |
|   |    |    | 3 | 16 | nil |    |
|   |    |    | 4 | 19 | nil |    |
|   |    |    | heel | 10 | 2140 |    |
| 3 | 100 | 135 | 1 | 31 | 50 | no |
|   |    |    | 2 | 21 | 50 |    |
|   |    |    | 3 | 19 | 90 |    |
|   |    |    | 4 | 15 | 200 |    |
|   |    |    | heel | 5 | 7360 |    |
| 4 | 100 | 135 | 1 | 29 | nil | yes |
|   |    |    | 2 | 31 | nil |    |

-continued

| RUN | PRESS (mm) | HEAD TEMP deg C. | CUT # | WT (g) | THA (ppm) | CAUSTIC ADDED |
|---|---|---|---|---|---|---|
| | | | 3 | 14 | nil | |
| | | | 4 | 17 | nil | |
| | | | heel | 3.7 | not available | | nil = the detection limit is about 20 ppm THA, and the integrator starts to assign THA at about 50 ppm.

Example 10

Removal of Methyltetrahydropyridine (MTHP) from 2-methylpentamethylenediamine (MPMD)

Two runs were made using 70 grams of MPMD containing 1900 ppm of MTHP. In one run, 0.1 grams of 50% sodium hydroxide (715 ppm NaOH based on MPMD) were added, and the mixture was heated for 30 min at 90 deg C. Distillation was then carried out as in the case of the HMD run above. The control run (run 1) contained no caustic.

| RUN | PRESS (mm) | HEAD TEMP deg C. | CUT # | WT (g) | MTHP (ppm) | CAUSTIC ADDED |
|---|---|---|---|---|---|---|
| 1 | 20 | 85 | 1 | 24 | 1880 | no |
| | | | 2 | 22 | 2080 | |
| | | | 3 | 21 | 1890 | |
| | | | 4 | 2 | 1290 | |
| | | | heel | 1 | 1180 | |
| 2 | 20 | 85 | 1 | 14 | 50 | yes |
| | | | 2 | 16 | 30 | |
| | | | 3 | 17 | nil | |
| | | | 4 | 13 | 90 | |
| | | | heel | 2 | not available | |

MTHP has the formula:

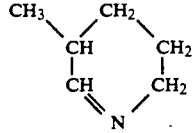

Example 11

Removal of Mono-Unsaturated Cyclododecylamine (CDDI) 1,12-Dodecanediamine

The same procedure was used here as was used for the MTHP/MPMD case. The starting dodecanediamine contained 340 ppm CDDI.

| RUN | PRESS (mm) | HEAD TEMP deg C. | CUT # | WT (g) | THA (ppm) | CAUSTIC ADDED |
|---|---|---|---|---|---|---|
| 1 | 0.3 | 110 | 1 | 21 | 40 | yes |
| | | | 2 | 16 | 10 | |
| | | | 3 | 17 | 20 | |
| | | | 4 | 2 | 20 | |
| | | | heel | 6 | not available | |
| 2 | -0.3 | 110 | 1 | 17 | 50 | no |
| | | | 2 | 13 | 20 | |
| | | | 3 | 15 | 50 | |
| | | | 4 | 12 | 100 | |
| | | | heel | 8 | 490 | |

CDDI has the formula:

I claim:

1. A process for separating an aliphatic aminonitrile or diamine having 4 to 12 carbon atoms from a mixture consisting essentially of a cyclic, aliphatic, mono-unsaturated amine having a corresponding number of carbon atoms, said aliphatic aminonitrile being selected from the group consisting of 4-aminobutyronitrile, 5-aminovaleronitrile, 2-methyl-5-aminovaleronitrile, 6-aminocapronitrile, 12-aminododecanenitrile, said diamine being selected from the group consisting of 1,4-tetramethylenediamine, 1,5-pentamethylenediamine, 2-methyl-1,5-pentamethylenediamine, 1,6-hexamethylenediamine, 1,12-dodecanediamine, and said cyclic, aliphatic mono-unsaturated amine being selected from the group consisting of dihydropyrrole, tetrahydropyridine, 2-methyltetrahydropyridine, tetrahydroazepine, and mono-unsaturated cyclododecylamine, which consists essentially of adding a caustic compound to the mixture in the amount in the range of about 0.025% by weight to an amount about 5% in excess of the stoichiometric amount of the cyclic, aliphatic, mono-unsaturated amine in the mixture, and then distilling the aliphatic aminonitrile or diamine from the mixture at a temperature less than about 170 degrees C. and at a pressure less than atmospheric.

2. The process of claim 1 in which the caustic compound is selected from the group consisting of alkali metal hydroxides, tetraalkylammonium hydroxides, alkaline earth hydroxides, alkali metal alkoxides and alkaline earth metal alkoxides.

3. The process of claim 1 in which the pressure used in the distillation is less than about 100 mm of mercury.

* * * * *